(12) United States Patent
Wesseler (10) Patent No.: US 9,687,645 B2
(45) Date of Patent: Jun. 27, 2017

(54) LUER LOCK CONNECTOR WITH GROOVES

(71) Applicant: B. BRAUN AVITUM AG, Melsungen (DE)

(72) Inventor: Matthias Wesseler, Melle (DE)

(73) Assignee: B. BRAUN AVITUM AG, Melsungen (DE)

( * ) Notice: Subject to any disclaimer, the term of this patent is extended or adjusted under 35 U.S.C. 154(b) by 138 days.

(21) Appl. No.: 14/295,429

(22) Filed: Jun. 4, 2014

(65) Prior Publication Data

US 2014/0378915 A1    Dec. 25, 2014

(30) Foreign Application Priority Data

Jun. 24, 2013   (DE) .......................... 10 2013 106 550

(51) Int. Cl.
*A61M 39/16* (2006.01)
*A61M 39/12* (2006.01)
(Continued)

(52) U.S. Cl.
CPC ............ *A61M 39/16* (2013.01); *A61M 39/12* (2013.01); *A61M 39/20* (2013.01); *A61J 1/2027* (2015.05);
(Continued)

(58) Field of Classification Search
CPC ...... A61M 39/16; A61M 5/14; A61M 5/1413; A61M 1/0086; A61M 39/10;
(Continued)

(56) References Cited

U.S. PATENT DOCUMENTS

| 5,534,228 A * | 7/1996 | Wesseler ............... A61M 39/10 422/541 |
| 7,905,873 B2 * | 3/2011 | Rondeau ............. A61M 39/221 251/142 |

(Continued)

FOREIGN PATENT DOCUMENTS

| DE | 39 26 395 | 3/1991 |
| DE | 41 14 246 | 11/1992 |

(Continued)

OTHER PUBLICATIONS

European Search Report for EP 14172543 issued Oct. 23, 2014.
German Search Report for DE 10 2013 106 550.3 dated Sep. 2, 2013.

*Primary Examiner* — Imani Hayman
*Assistant Examiner* — Nilay Shah
(74) *Attorney, Agent, or Firm* — RatnerPrestia (57) ABSTRACT

Connector systems for a fluid container for pharmaceutical solutions are disclosed. The systems include an outer part adapted for insertion into a fluid conducting system and an inner part arranged in said outer part. The outer part includes a tamper-evident closure connected thereto at a predetermined breaking point that can be manually removed. An external side of the inner part abuts an internal side of the outer part. A closure element attached to the inner part prevents a flow of fluid through the inner part. The inner part and the outer part having provided thereon at least one fluid conducting element, such as a furrow, a flute, a depression or a groove. Medical supply systems comprising a bag, such as a dialysis bag, having such systems are also described.

14 Claims, 9 Drawing Sheets

(51) Int. Cl.
   *A61M 39/20*   (2006.01)
   *A61M 5/14*    (2006.01)
   *A61M 1/00*    (2006.01)
   *A61M 39/10*   (2006.01)
   *A61J 1/20*    (2006.01)

(52) U.S. Cl.
   CPC ......... *A61M 1/0086* (2014.02); *A61M 5/1413* (2013.01); *A61M 2039/1061* (2013.01)

(58) Field of Classification Search
   CPC .. A61M 2039/1027; A61M 2039/1061; A61M 2039/1005; A61M 2039/222; A61J 1/2027; A61J 1/2048
   See application file for complete search history.

(56) References Cited

U.S. PATENT DOCUMENTS

| | | | |
|---|---|---|---|
| 2008/0077063 A1* | 3/2008 | Meyer | A61H 9/0078 |
| | | | 601/148 |
| 2010/0151570 A1 | 6/2010 | Kader et al. | |
| 2011/0166532 A1 | 7/2011 | Brandenburger et al. | |

FOREIGN PATENT DOCUMENTS

| | | |
|---|---|---|
| DE | 43 13 636 | 10/1994 |
| DE | 10 2008 048988 | 4/2010 |
| DE | 10 2010 032 179 | 1/2012 |
| DE | 10 2011 016 977 | 10/2012 |
| EP | 1 859 773 | 11/2007 |
| EP | 2 257 334 | 12/2010 |
| WO | WO 2007/149960 | 12/2007 |

* cited by examiner

LUER LOCK CONNECTOR WITH GROOVES

CROSS REFERENCE TO RELATED APPLICATIONS

This application claims priority to German application DE 10 2013 106 550.3 filed Jun. 24, 2013, the contents of such application being incorporated by reference herein.

FIELD OF THE INVENTION

The present invention relates to a connector system or connection system for a fluid container for pharmaceutical solutions, comprising an outer part, which is adapted to be inserted into a fluid conducting system such as a hose or a bag spout, and an inner part arranged in said outer part and materially separate therefrom, wherein the outer part has provided thereon a tamper-evident closure, which is connected thereto at a predetermined breaking point and which can be torn off by manual force, wherein the inner part further abuts, at least sectionwise, with an external side thereof on an internal side of the outer part, and wherein, in addition to the tamper-evident closure, a closure element attached to the inner part prevents a flow of fluid through the inner part. The present invention also relates to a medical supply system, comprising a bag, such as a dialysis bag, having a connector system according to the present invention integrated or inserted therein.

BACKGROUND

In the field of medical technology, but also in other fields, e.g. for laboratory work, it is often necessary to transfer fluid in a specific sequence from one container to the next and to transfer it then after a specific period of time or a predetermined sequence of operations, e.g. after mixing or after a chemical reaction, somewhere else. As an example, reference is made to dialysis according to the hemofiltration method. There, e.g. a bicarbonate electrolyte solution is used as a replacement fluid.

Dialysis bag connections should here normally be kept available for guaranteeing efficient closure in combination with easy openability.

DESCRIPTION OF THE RELATED ART

The prior art, e.g. DE 43 13 636 C1, discloses a connector system for connecting fluid containers. This publication discloses e.g. a connector system for connecting fluid containers with medical fluids as well as one of the fluid containers to a transfusion set or a further container, the connector system connecting a first and a second connecting piece to a respective first connector so as to observe a predetermined connection sequence. The connectors are configured for connection to respective additional connectors provided on specific fluid containers. Connecting the two connecting pieces to one another is made possible. An intermediate piece with two interconnected connectors is here disclosed, the first one of said connectors being configured for releasable connection to the second connector of the first connecting piece as well as to a connection piece of the transfusion set and the second one being configured for non-releasable connection to the second connector of the second connecting piece. Before the connection to the second connecting piece is established, the intermediate piece is arranged in the interior of the first connecting piece.

A similar prior art is also known from DE 41 14 246 C2. There, a connector for a pharmaceutical solution container provided with a tubular connection part is presented, the connector comprising a first coupling part, which is adapted to be inserted in the connection part and which includes a first flow passage, and a second coupling part, which is adapted to be inserted in said first coupling part, said second coupling part including a second flow passage and being connected to a flexible pipe, and further comprising a shut-off element. It is here worth noting that the first coupling part is closed by an elastomeric stopper at the insertion opening, a sealing closure cap, provided with a frangible closure closing the central opening thereof, being positioned on top of the elastomeric stopper, and the central opening having locking projections for the second coupling part, which is insertable therein and on which projections are provided that correspond to said locking projections.

The prior art additionally discloses closure elements after the fashion of frangible cross members, such infusion bags being produced from a soft PP composite film.

SUMMARY OF THE INVENTION

The present invention intends to provide a dialysis bag with a frangible cross member/breakaway cross member and a tamper-evident closure, the frangible cross member serving, in turn, as a tamper-evident closure and being installed in the direction of the bag and supplemented by a further breakaway (twist-off) tamper-evident closure for sealing a luer inner cone in a sterile-tight manner.

Up to now, a luer connection area has normally been closed by a screw cap. Such screw caps, however, are disadvantageous insofar as they do not provide a completely tight closure during superheated steam sterilization. The result is that the connection luer inner cone fills with condensate, i.e. water, from the sterilization process. This, however, should be avoided.

The present invention further intends to provide a hose connector with a bag-side frangible cross member as a sterility closure, in the case of which the luer cone interior facing the user side is closed off from the external atmosphere in a sterile-tight manner and the sealed space is sterilizable.

According to the present invention, an object is achieved in that the inner part and the outer part have provided between them at least one fluid conducting element, such as a furrow, a flute, a depression or a groove, which extends over a certain length. By dimensioning the fluid conducting element such that it has a capillary effect, a sterilizing agent, such as steam, can also be conducted between the inner part and the outer part, in particular in a connection space in the interior of the inner part.

This is advantageous especially for the purpose of assembly, since air is allowed to escape. The fluid conducting elements are dimensioned such that they prevent dripping, but they are not sterile-tight. Furthermore, they prevent rotation of the inner part relative to the outer part.

Hence, a luer lock connector is provided, which is suitable for hose systems and adapted to be used in the case of bags, which are, or are to be provided with a tamper-evident closure. An internal space therein can then be sterilized. Steam can be conducted into the internal space via capillary grooves, i.e. formations of the fluid conducting elements. A closure element configured like a frangible cross member closure and oriented in the direction of the bag allows free removal of the content.

The inner part, which can also be referred to as lower part, is provided with one or a plurality of axially extending capillary grooves on the outer circumferential surface thereof. These grooves are configured such that, when attached to the outer part, which may also be referred to as upper part, the inner part has/establishes a capillary connection allowing steam, air or fluid to enter the interior of the mounted closure.

As has already been mentioned, this guarantees, on the one hand, an escape of air from the internal space of the component during mounting and, on the other hand, steam is allowed to flow into the internal space during steam sterilization, whereby sufficient sterilization will be guaranteed.

In other words, the interior of the connector can be sealed in a sterile-tight manner, the space between the inner and the outer part can be included in the sterilization process, sterile-tight sealing of the luer cone can be accomplished and a frangible cross member can be utilized for allowing a flow through the connector system.

A luer lock connection with a sterile-tight tamper-evident closure of the luer inner cone, a sterile-tight interior of the whole connector and a frangible cross member closure for allowing a flow of media are thus realized.

It will, for example, be of advantage when a plurality of fluid conducting elements is provided, preferably four, five, six, seven, eight, nine, ten, eleven, twelve or more fluid conducting elements. Two or three fluid conducting elements may, however, be used as well. A uniform penetration of the gap area between the inner part and the outer part can thus be accomplished, whereby good sterilization will be achieved.

As regards the sterilization effect, it will be advantageous when the fluid conducting elements are uniformly distributed over the circumference of the inner part and extend straight or in a curved shape. The fluid conducting elements may, of course, also be uniformly distributed over the inner circumference of the outer part and may extend also there straight or in a curved shape. A straight shape is advantageous insofar as it is easy to manufacture, whereas a curved, in particular a thread-like or helical shape of the fluid conducting elements offers other advantages.

An advantageous embodiment is also characterized in that fluid conducting elements are formed in the outer circumferential surface/outer surface of the inner part and/or in the inner circumferential surface/inner surface of the outer part. It is even possible that one fluid conducting element is formed in the outer circumferential surface, i.e. the outer surface of the inner part and another fluid conducting element is formed in the inner circumferential surface, i.e. the inner surface of the outer part and that, considering the whole circumference, the fluid conducting elements are adequately distributed.

It proved to be expedient, when the outer part has an inner circumferential surface determined by a cylinder and/or the inner part has an outer circumferential surface determined by a cylinder. The inner or outer part can then be configured as a hollow cylinder, with only one of the two surfaces of one of the two parts being cylindrical in shape.

The fluid conducting elements may extend from an end of the outer part facing away from the tamper-evident closure to an end of the outer part facing the tamper-evident closure such that fluid flows to the inner side of the tamper-evident closure and/or of the closure element. Utilizing the capillary effect, sterilizing agent can thus also be effective in the area between the tamper-evident closure and the closure element, i.e. the interior of the inner part/combination of the internal space in the tamper-evident closure and the internal space of the inner part (i.e. the connection space).

For providing compatibility with other system elements, it will be of advantage when the outer part is configured like a luer cone on the external side thereof and/or the inner part is configured like a luer cone on the internal side thereof. It will also be advantageous when, on the side of the outer part facing the tamper-evident closure, a luer lock external thread or a luer slip extension is provided.

When the tamper-evident closure is configured as a wing-shaped handle, the connector system can be opened on one side by simple means, e.g. by utilizing human manual force. Alternatively or additionally it will also be of advantage when the closure element is configured as a frangible cross member connected to a predetermined breaking point. Such frangible cross members can also be operated by applying the normal force of a finger or fingers through a bag connection or a hose, and cause the connector system on the other side to be opened.

For making the frangible cross member easily accessible, it will be of advantage when the frangible cross member is connected to the inner part at an inner part end facing away from the tamper-evident closure.

It will also be of advantage when the inner part is secured in position on the outer part via a form-fit connection, a force-fit connection and/or a substance-to-substance bond, such as a welded joint, an adhesive joint, a joint established by pressing, a snap joint, e.g. with an undercut and/or a circumferentially extending spring.

An advantageous embodiment is also characterized in that a depression defined by the fluid conducting element has a depth which, measured in the radial direction, is smaller than a thickness of the wall of the outer part and/or the inner part.

Such an embodiment can be further developed in an advantageous manner, when the depth does not change over the length of the fluid conducting element or when it varies continuously or abruptly. When, for example, the depth varies continuously after the fashion of a progressive or degressive curve, certain advantageous effects can be accomplished.

An advantageous embodiment is also characterized in that the depth is too small for causing a complete perforation of the inner part or of the outer part. The integrity of the connector system is thus not at risk.

It will also be of advantage when the inner part is sealingly press-fitted into the outer part. This is a particularly simple mode of connecting the inner part to the outer part, which is favored for reasons of cost reduction.

It is thus possible to provide a hose closure comprising a partially cylindrical inner part, which is provided with a luer hollow cone in the interior thereof and which is open on one end and closed on the closed end with a frangible cross member for opening the duct. This cylindrical inner part is sealingly press-fitted into a complementary outer part. The outer part is cylindrical in the interior thereof for receiving therein the above-described inner part. In addition, the outer part is equipped with an external thread according to the Luer Standard.

Above the thread convolutions, a predetermined breaking point in the form of a thin circumferentially extending wall is arranged. Above this predetermined breaking point, a wing-shaped handle is provided, which is used for shearing off the predetermined breaking point by a twisting movement thus uncovering the luer inner cone.

This composite unit comprising the inner and the outer part can be sterilized, e.g. in advance, by high energy radiation (e.g. gamma radiation) or in the installed condition by superheated steam sterilization. For the purpose of superheated steam sterilization, the inner wall of the outer part or the outer wall of the inner part may be provided with axially parallel flutes so that the fluid contained in the bag or the vapor of this fluid will be able to flow into the spaces between the inner and the outer part.

A stable connection between the inner part and the outer part can be established e.g. by pressing, by snap-locking, making e.g. use of an undercut and a circumferentially extending spring, a welded joint, an adhesive joint or other connecting modes.

The operating sequence is characterized in that, at the outer end of the luer connector press-fitted in the bag hose connection, the luer inner cone of the luer connector is exposed by twisting off the tamper-evident closure. A consumer is connected via a male luer lock connection by screwing on. The frangible cross member in the bag hose is broken away at an adequate moment in time. The content of the bag then flows to the consumer.

BRIEF DESCRIPTION OF THE DRAWINGS

The invention is best understood from the following detailed description when read in connection with the accompanying drawings. Included in the drawings are the following figures:

FIG. 8 shows an enlarged representation of area VIII of FIG. 7.

DETAILED DESCRIPTION OF THE PREFERRED EMBODIMENTS

The figures are only of a schematic nature and they only serve to make the invention more easily understandable. Identical elements are identified by identical reference numerals.

The individual features of the embodiments may also be combined with one another and/or substituted for one another.

Figure 1:
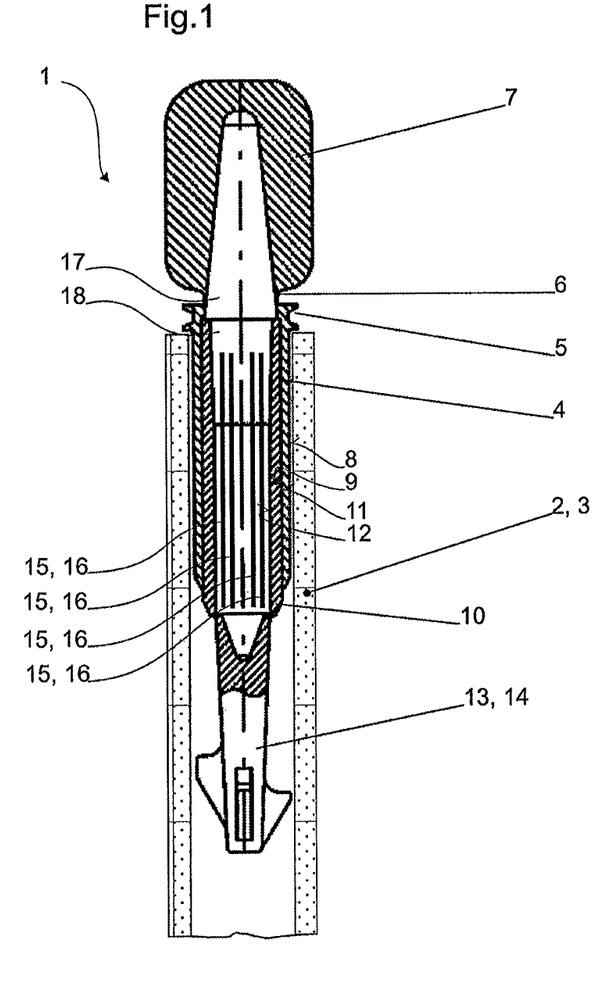
FIG. 1 shows a connector system according to the present invention in a longitudinal section view.

In FIG. 1 a first embodiment of a connector system 1 according to the present invention is shown.

Figure 14:
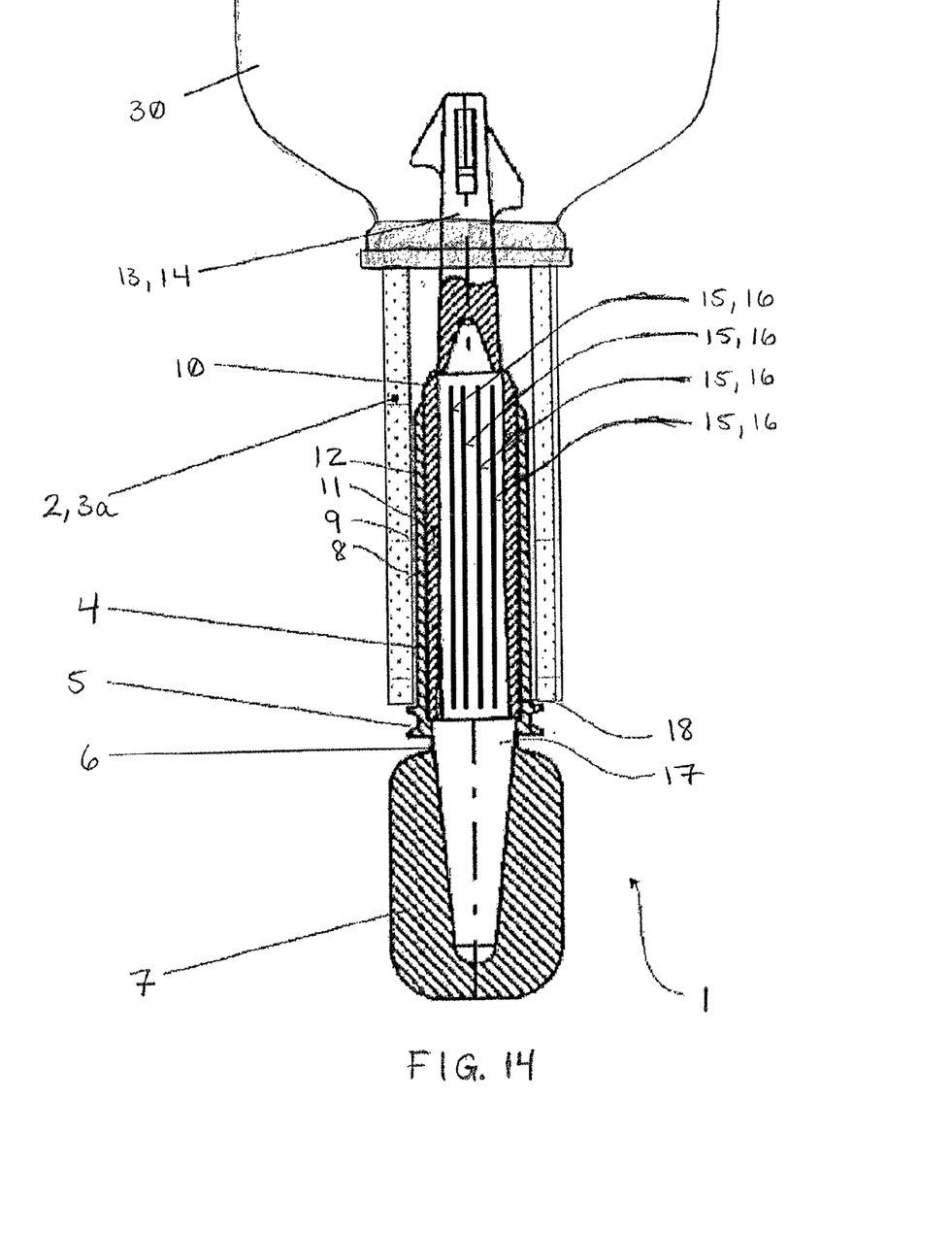
FIG. 14 shows a medical supply system having a connector system in use with a fluid container in accordance with aspects of the present invention.

The connector system is provided for use on a fluid container 30 (see FIG. 14), said fluid container 30 being adapted to keep pharmaceutical solutions therein. The fluid container 30 may be a fluid bag. The connector system 1 is inserted in a fluid conducting system 2. The fluid conducting system 2 is configured as a hose 3. It may, however, also be configured as a hose section or as a bag spout 3a (see FIG. 14).

Figure 15:
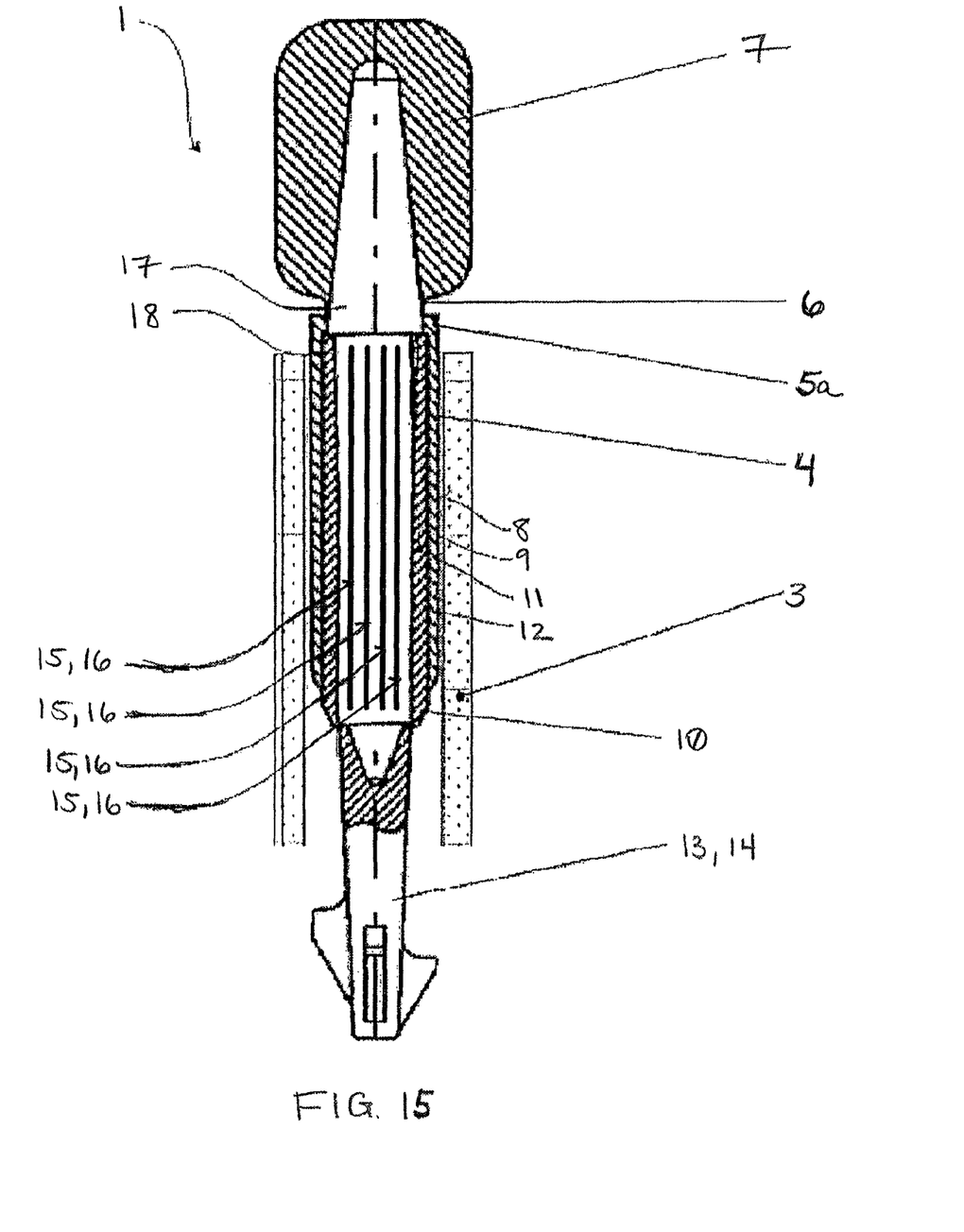
FIG. 15 shows a variant of an assembled connector system with a luer slip extension in accordance with aspects of the present invention.

The connector system 1 comprises an outer part 4 and its external shape complies with the well-known Luer Standard. A luer lock external thread 5 or a luer slip extension 5a without an external thread (see FIG. 15) may be provided on a central area or on an area located close to the end. The luer lock external thread 5 or luer slip extension 5a is followed by a predetermined breaking point 6 allowing an embodiment of a tamper-evident closure 7, which is there connected thereto and configured like a wing-shaped handle, to be torn off the outer part 4. The outer part 4 has an external side 8 and an internal side 9. The outer part 4 has inserted therein an inner part 10, which is also secured in position with an interference fit and which also has an external side 11 and an internal side 12. The external side 8 of the outer part 4 may also be referred to as outer circumferential surface or outer surface. The internal side 9 of the outer part may also be referred to as inner circumferential surface or inner surface. The external side 11 of the inner part 10 may also be referred to as outer circumferential surface or outer surface. The internal side 12 of the inner part 10 may also be referred to as inner circumferential surface or inner surface.

On the connector system side facing away from the tamper-evident closure 7, i.e. on the other end of the connector system 1, a closure element 13 is provided. The closure element 13 is configured as a frangible cross member 14.

The inner part 10 is inserted in the outer part 4 concentrically therewith.

The outer part 4 has a luer cone on its external side 8. Also the inner part 10 has a luer cone on its internal side 12, i.e. a luer inner cone.

Figures 2, 3:
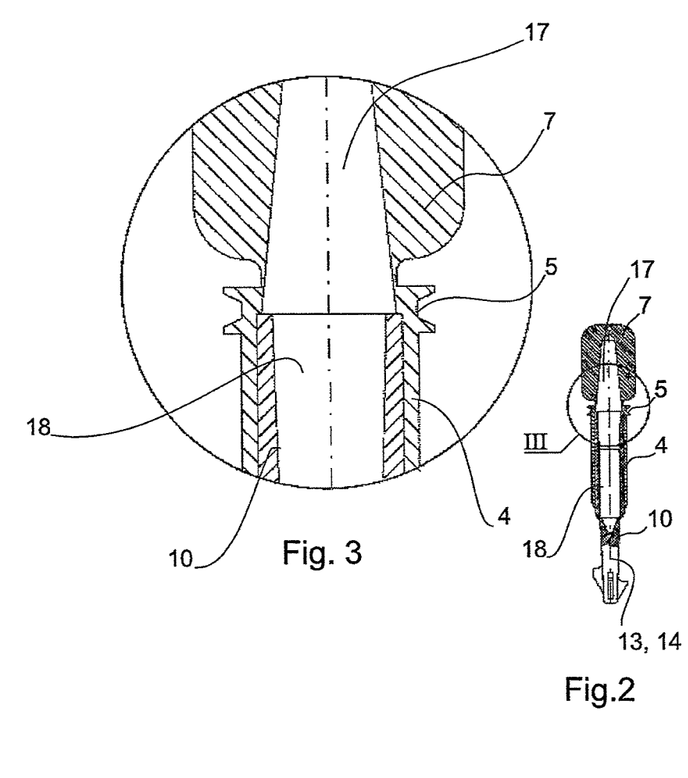
FIG. 2 shows a variant of an assembled connector system.
FIG. 3 shows an enlarged representation of area III of FIG. 2.
Figures 4, 5:
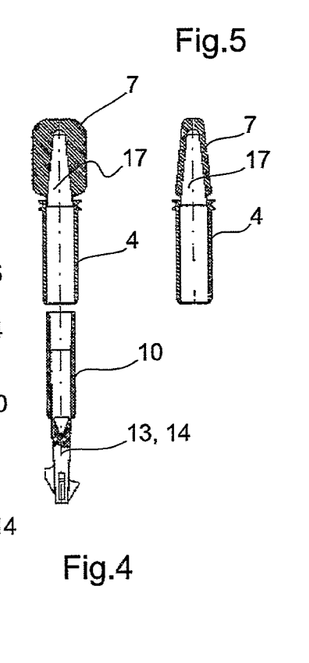
FIG. 4 shows the still separate inner and outer parts of the connector system in a condition in which it is not installed in a fluid system.
FIG. 5 shows a variant of an outer part for a connector system according to the present invention.
Figure 6:
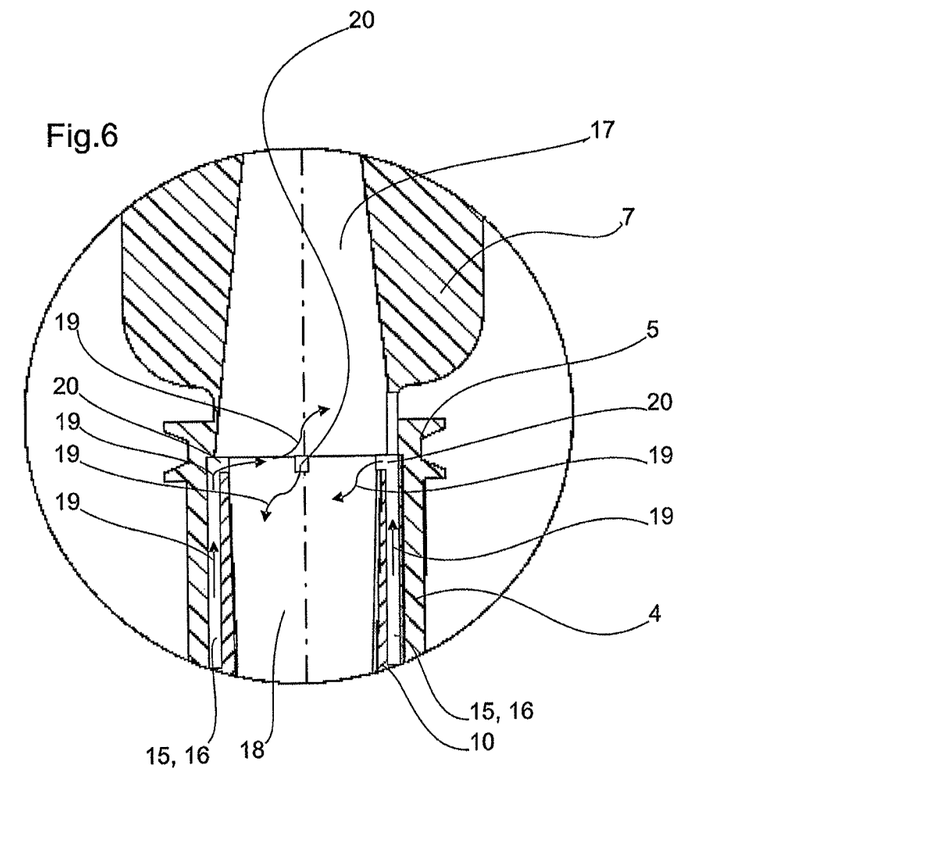
FIG. 6 shows an enlarged representation of a connector system area corresponding to FIG. 3, the longitudinal section being here made in the area of the flutes defining the fluid conducting elements and this area being shown as VI in FIG. 7 in the overall context, FIG. 7 a connector system of the type disclosed by the present invention in a view showing a longitudinal section through the fluid conducting elements.
Figures 7, 8:
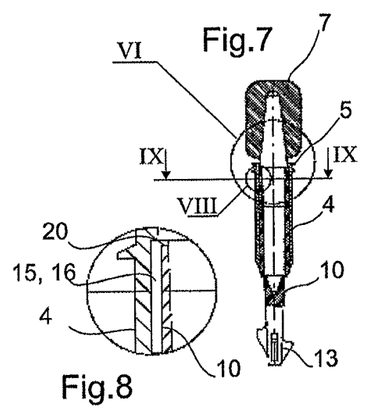
Figure 9:
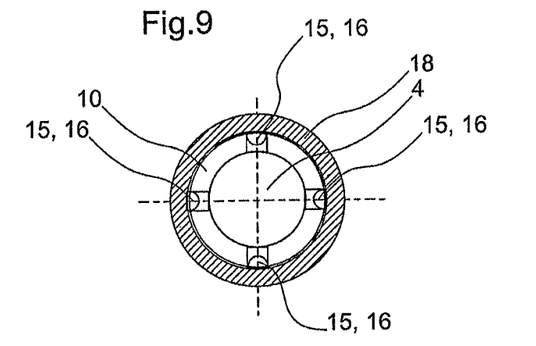
FIG. 9 shows a cross-section transversely to the longitudinal axis of the connector system of FIG. 7.
Figure 10:
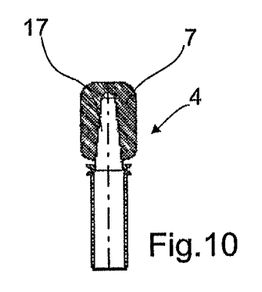
FIG. 10 shows in a longitudinal section view only the outer part of the connector system of FIG. 7.
Figure 11:
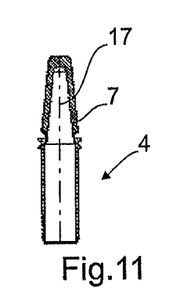
FIG. 11 shows a variant of the outer part of the connector system of FIG. 7.
Figure 12:
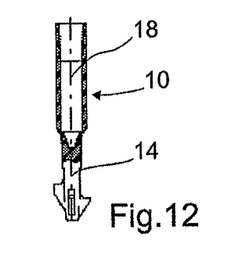
FIG. 12 shows the inner part of the connector system of FIG. 7.
Figure 16:
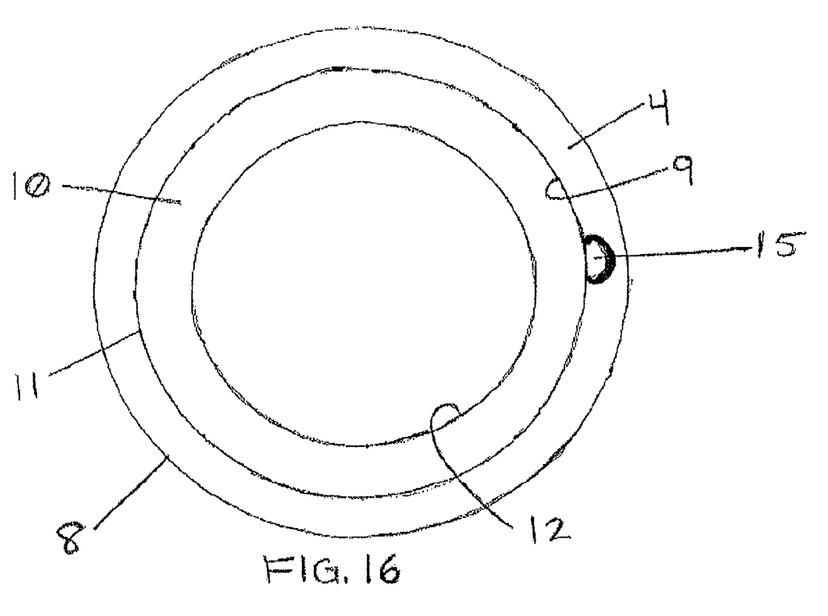
FIG. 16 shows a representation of fluid conducting elements formed in an inner circumferential surface/inner surface of an outer part in accordance with aspects of the present invention.
Figure 17:
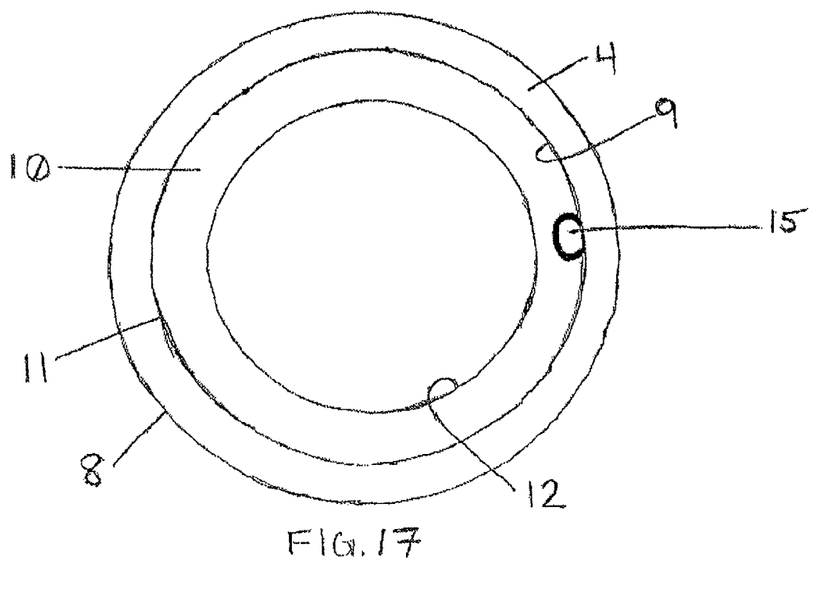
FIG. 17 shows a representation of fluid conducting elements formed in an outer circumferential surface/outer surface of an inner part in accordance with aspects of the present invention.
Figure 18:
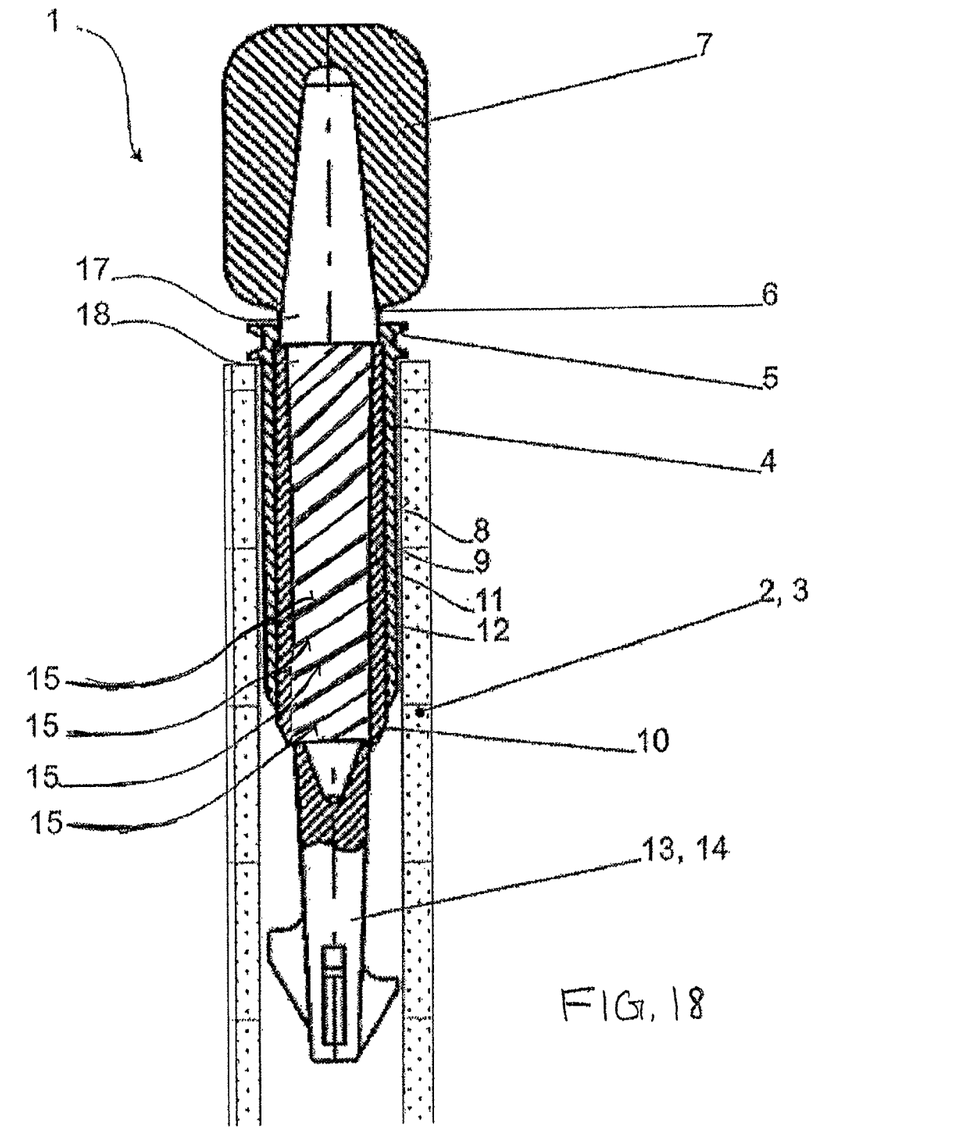
FIG. 18 shows a connector system having fluid conducting elements arranged in a helical shape in accordance with aspects of the present invention.

Between the inner part 10 and the outer part 4, fluid conducting elements 15 are provided. The fluid conducting elements 15 may be formed in the inner circumferential surface/internal side 9 of the outer part 4 (see FIG. 16) and/or the outer circumferential surface/external side 11 of the inner part 10 (see FIG. 17). The fluid conducting elements 15 may be configured like straight longitudinal flutes 16. The fluid conducting elements 15 may also be configured in a curved shape, for example, in a helical shape (see FIG. 18) or a thread-like shape. FIG. 2 shows the assembly of the inner part 10 and of the outer part 4. The area of the luer lock external thread 5 is shown in an enlarged representation in FIG. 3. Also an internal space 17 in the tamper-evident closure 7 can clearly be seen here. This internal space 17 merges with an internal space 18 of the inner part 10. Whereas FIG. 4 still shows the two non-assembled inner and outer parts 10 and 4, FIG. 5 only shows the outer part 4 with a modified shape of the tamper-evident closure. The wings are here smaller. Such a longitudinal section will, however, also be obtained, when wings, which are located in the same plane, project from only two sides of a tamper-evident closure 7 and when the longitudinal section is utilized in a position oriented transversely, preferably orthogonally thereto.

FIGS. 6 to 12 make it easier to understand how the fluid conducting element 15 is oriented in space. It can, for example, clearly be seen that the longitudinal flutes 16 extend up to and into the area of the luer lock external thread 5 and allow a flow of sterilizing agent symbolized with arrows 19. The longitudinal flutes 16 comprise an aperture 20, which is directed radially inwards and which leads into the internal space 18 of the inner part 10, the aperture having a cross-section after the fashion of a polygon, in particular a quadrangle, a rectangle or a square. As can be seen in a particularly clear manner in FIG. 9, the longitudinal flutes 16 are concave in shape with a partially circular/semicircular cross-section.

Figure 13:
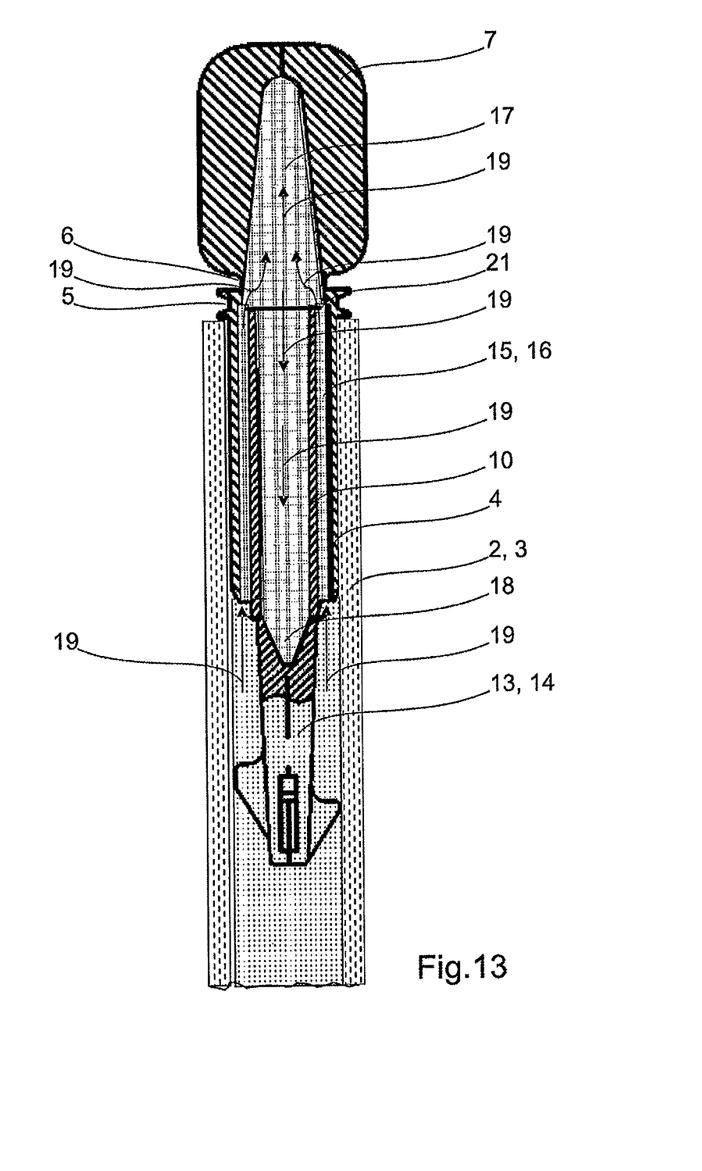
FIG. 13 shows a schematic representation of the fluid flow through a connector system according to the present invention.

Also FIG. 13 shows a connector system 1 within the framework of a luer lock connector with a tamper-evident closure 7 and a frangible cross member 14 for hose connections, a flow of sterilizing agent being again marked by arrows 19. Other than in the embodiments according to FIGS. 6 to 12, this embodiment does, however, not comprise any apertures 20, but outlets 21 corresponding directly to the internal space 17 of the tamper-evident closure 7.

The longitudinal flutes 16 are configured like capillary lines or capillaries.

The invention claimed is:

1. A connector system for a fluid container for pharmaceutical solutions, comprising:
    an outer part having an inner circumferential surface and an outer circumferential surface, the outer part adapted to be inserted into a fluid conducting system; and
    an inner part having an outer circumferential surface and an inner circumferential surface, the inner part arranged in said outer part and materially separate therefrom;
    wherein the outer part has provided thereon a tamper-evident closure, which is connected thereto at a predetermined breaking point and which can be torn off by manual force, wherein the outer circumferential surface of the inner part further abuts, at least sectionwise, with the inner circumferential surface of the outer part, wherein, in addition to the tamper-evident closure, a closure element attached to the inner part prevents a flow of fluid through the inner part, and wherein the inner part and the outer part have provided therein at least one fluid conducting element wherein the at least one fluid conducting element is formed within at least one of the outer circumferential surface of the inner part or the inner circumferential surface of the outer part as at least one of a furrow, a flute, a depression, or a groove, wherein the at least one fluid conducting element is formed between the outer circumferential surface of the inner part and the inner circumferential surface of the outer part, wherein the at least one fluid conducting element does not perforate through the inner part from the inner circumferential surface of the inner part to the outer circumferential surface of the inner part, and wherein the at least one fluid conducting element does not perforate through the outer part from the inner circumferential surface of the outer part to the outer circumferential surface of the outer part.

2. The connector system according to claim 1, wherein a plurality of fluid conducting elements is provided.

3. The connector system according to claim 2, wherein the plurality of fluid conducting elements are uniformly distributed over the outer circumferential surface of the inner part and extend straight or in a curved shape.

4. The connector system according to claim 1, wherein the inner circumferential surface of the outer part is cylindrical.

5. The connector system according to claim 1, wherein the outer part is configured as a luer cone on an external side thereof.

6. The connector system according to claim 1, wherein, on a side of the outer part facing the tamper-evident closure, a luer lock external thread or a luer slip extension is provided.

7. The connector system according to claim 1, wherein the tamper-evident closure is configured as a wing-shaped handle.

8. A medical supply system, comprising a fluid bag having the connector system according to claim 1 integrated or inserted therein.

9. The system of claim 8, wherein the fluid bag is a dialysis bag.

10. The connector system according to claim 1, wherein the fluid conducting system is a hose or a bag spout.

11. The connector system according to claim 1, wherein the outer circumferential surface of the inner part is cylindrical.

12. The connector system according to claim 1, wherein the inner part is configured as a luer cone on an internal side thereof.

13. The connector system according to claim 1, wherein the closure element is configured as a frangible cross member connected to a predetermined breaking point.

14. The connector system according to claim 13, wherein the frangible cross member is connected to the inner part at an inner part end facing away from the tamper-evident closure.

* * * * *